United States Patent [19]
Grossman et al.

[11] Patent Number: 5,156,974
[45] Date of Patent: Oct. 20, 1992

[54] METHOD FOR DETERMINING THE FIBRINOGEN LEVEL OF A BLOOD SAMPLE

[75] Inventors: Hyman Grossman, Lambertville, N.J.; Michael Rausch, Warrington, Pa.

[73] Assignee: Biodata Corporation, Hatboro, Pa.

[21] Appl. No.: 199,551

[22] Filed: May 27, 1988

[51] Int. Cl.$^5$ ............................................. G01N 33/86
[52] U.S. Cl. .................................... 436/69; 436/171; 436/805; 435/4; 435/13; 73/64.43; 364/413.09; 356/39
[58] Field of Search ............... 436/63, 69, 86, 164, 436/171, 805; 435/4, 13; 73/64.1; 364/413.09; 356/39

[56] References Cited
U.S. PATENT DOCUMENTS 3,307,392 3/1967 Owen et al. .......................... 73/64.1
3,458,287 7/1969 Gross et al. .......................... 73/64.1
4,047,890 7/1977 Eichelberger et al. ........... 23/230 B
4,289,498 7/1981 Baughman et al. ............... 23/230 B

*Primary Examiner*—James C. Housel
*Assistant Examiner*—David Redding
*Attorney, Agent, or Firm*—Seidel, Gonda, Lavorgna & Monaco

[57] ABSTRACT

A method for determining the fibrinogen level of a patient blood plasma in an optical density based prothrombin time test. The method and apparatus utilize a novel parameter DELTA which factors out statistical inaccuracies associated with prior art test methods. The patient fibrinogen level is determined using DELTA points calculated from blood samples having known fibrinogen levels in the low, normal and high ranges. A piece wise function is then constructed around the DELTA points and the fibrinogen level of a patient blood sample is calculated using four equations prestored in a non-volatile memory.

3 Claims, 13 Drawing Sheets

METHOD FOR DETERMINING THE FIBRINOGEN LEVEL OF A BLOOD SAMPLE

BACKGROUND OF THE INVENTION

The present invention is directed to a method and apparatus for determining the level of fibrinogen in a blood sample. Specifically, the present invention is directed toward a method and microprocessor based apparatus for determining the level of fibrinogen in a sample using a piece-wise function which is generated empirically and pre-stored in a non-volatile memory.

The process of blood coagulation is complex. In general, it involves the generation of fibrin fibers which are formed by the polymerization of molecules of a protein called fibrinogen. Fibrinogen is catalyzed from an enzyme called thrombin, which is itself catalyzed from the enzyme prothrombin.

The prothrombin time test (PT test) is commonly used to determine the ability of a blood sample to clot. This test is extensively used in hospitals, clinics, and laboratories for pre-operative evaluations and for anti-coagulant therapy administered to cardiac patients, for example. The PT test is based upon the length of time required for a sample of plasma to clot under the influence of certain reagents. In the PT test, these reagents are calcium ion and thromboplastin. Thromboplastin is derived from the brain, lung, placenta and other tissues of humans, rabbits, cows, and other non-human species.

Methods for detecting the formation of fibrin clots date back to the late 1870's. Such early methods were manual. For example, in one test a white horse hair was drawn through a blood specimen. The end point of the clotting time was the point where shreds of fibrin could be visually detected on the hair.

By 1910, an electrical apparatus called a "Coagulo-viscosimeter" was developed for directly measuring the change in viscosity of a blood sample as it clots. The apparatus provided a direct indication of voltage which could be plotted against clotting time.

In the early 1920's, rudimentary photoelectric techniques were developed to detect variations in light transmissivity of a blood sample during clotting. An apparatus termed a "Nephelometer" was devised. This device consisted of a light source which furnished a constant illumination to a sample. During coagulation of the sample, variations in the optical transmissivity of the sample were registered by a thermopile connected to a sensitive galvanometer. By reading the movement of the galvanometer needle, transmissivity values could be plotted against elapsed time.

In the mid-1930's, investigations of the coagulation of blood plasma using more sophisticated photoelectric techniques were conducted. It was noted that an increase in optical density occurs as blood coagulates. The possibility of detecting this change by photoelectric techniques was investigated. This lead to the development of an instrument which displayed increasing density of the same as a gradual change in the voltage displayed by a galvanometer. In addition, a water bath was used to maintain the blood sample at 37° C.

Modern optical density detection systems operate on the principle that an increase in the optical density of a coagulating plasma sample will decrease the transmissivity of light through the sample. In a typical optical density detection system, a test blood plasma sample is placed in a transparent sample cuvette and reacted with a test reagent such as thromboplastin. Light or electromagnetic radiation in the visible or near-infrared spectrum is then passed through the plasma-reagent mixture as the sample clots. As the biochemical change leading to fibrin formation takes place within the sample, the optical density of the sample increases. Output voltages corresponding to the optical density of the sample and the rate of change in optical density of the sample with respect to time are outputted, and used to determine coagulation end points.

While the existence of the relationship between fibrinogen (fibrin) levels and optical density has long been recognized, there has been wide disagreement concerning the nature and proper methodology for measuring the relationship, and numerous test parameters have been devised for determining fibrinogen levels using optical density data.

Several prior art techniques focused upon determining an optical "end point" corresponding to the initiation of fibrin formation. U.S. Pat. Nos. 3,658,490 and 3,307,392, for example, disclosed a method and apparatus which generated a signal corresponding to the value of the first differential of optical density with respect to time at the point corresponding to the incipiency of fibrin formation. In the method and apparatus of U.S. Pat. No. 3,458,287, the second differential of optical density with respect to time was measured to determine the maximum value of the first differential optical density, a value also corresponding to a preselected optical density time point. Each of these tests therefore measured an optical "end point" related to the rate of fibrin clot formation.

The test methods discussed above contained several flaws. Most notably, the rate of fibrin formation, while clinically significant, is not always indicative of the fibrinogen level of the sample. Rather, it may be a function of a given sample's ability to produce thrombin, the material which converts fibrinogen to fibrin. Two samples having equal levels of fibrin may produce different optical density test curves if each sample produces thrombin at a different rate.

Some prior art systems attempted to compensate for this fact by focusing on an absolute change in the optical density of a sample between a pre-clot or initial state and a preselected final state. While such systems eliminate the inaccuracies caused by factors such as differences in the thrombin levels between respective samples, they incorrectly assumed a uniformity in the initial optical densities of pre-clotted samples. Some blood samples, for example, may be cloudy due to the presence of lipid, which will alter the initial optical density of the sample. A system which solves some of these problems has been developed by Ortho Diagnostic Systems, Inc. of Raritan, N.J. The Ortho Diagnostic system adjusts the intensity of the light source between samples. However, the Ortho Diagnostics system does not provide a clinically acceptable parameter linking a coagulation end point or optical density data with fibrinogen levels.

In addition to the empirical problem of choosing clinically significant optical end points for determining the levels of fibrinogen using optical density data, prior art methods and apparatus further incorrectly assume that the relationship between changes in optical density and fibrinogen level is linear. See, U.S. Pat. No. 4,289,498. Prior art systems which assume a purely linear relationship between optical density change and fibrinogen levels have typically determined fibrinogen levels by constructing a best fit linear approximation using a plurality of optical density data points calculated from samples having fibrinogen levels within the normal range.

Linear approximation methods, while accurate predictors of fibrinogen levels in the normal range, are characterized by two basic problems. First, such methods typically do not produce best fit linear approximations which intercept both axes at the origin. In theory and practice, however, a plasma sample having a zero fibrinogen level cannot clot, and therefore cannot exhibit any change in optical density. This fact plainly suggests that the theoretical endpoint of any fibrinogen versus optical density time graph must be centered at the origin and raises doubts as to the accuracy of low fibrinogen levels calculated using linear best fit approximations.

Second, the linear relationship between change in optical density and fibrinogen levels also breaks down at fibrinogen levels significantly above the normal range. Most methods which utilize linear best fit approximations, utilize linear extrapolation above the normal, producing lines which suggest the theoretically impossible result of an optical density greater than complete opaqueness. Plainly, fibrinogen levels determined using conventional best fit linear approximations are not always accurate.

It is therefore the principal object of the method and microprocessor based apparatus of the present invention to resolve the problems associated with prothrombin time (PT) and other blood coagulation tests utilizing prior art optical density fibrinogen methods.

The present invention performs the PT test in association with a novel parameter designated as DELTA, which compensates for the inaccuracies associated with prior art optical density systems based on linear best fit approximations. DELTA in the present invention is defined as the ratio of an output voltage corresponding to the pre-clot optical transmissivity voltage level (PCOV) minus a special end of reaction term corresponding to a transmission voltage measured at the time when the rate of change in optical density decreases to one-half of its previous maximum value (ACOV), the difference being divided by (PCOV);

$$DELTA = (PCOV - ACOV)/PCOV$$

ACOV represents a point on the optical transmissivity time curve at which almost all clot formation activity is complete and remaining clot formation proceeds in a predictable fashion. Thus, differences in reaction rates between different blood plasma samples have minimal effect on the ACOV measurement. Further, because the difference of the numerator is divided by pre-clot voltage (PCOV), inaccuracies caused by differences in pre-clotting optical densities are factored out of the equation.

The relationship between the DELTA parameter and fibrinogen level is then directly determined from a piecewise function constructed using three DELTA points calculated from preselected reference samples having known low, normal and high fibrinogen levels which are stored in a non-volatile memory and used in association with one of four equations pre-stored in a non-volatile memory. The unknown fibrinogen level of a patient blood sample is calculated by the microprocessor using one of the four pre-stored equations which utilize the pre-stored reference fibrinogen values and their corresponding DELTA values.

The piece-wise function of the present invention provides accurate results for patient blood samples having low, normal and high fibrinogen levels. The present invention thus provides a method and apparatus for accurately determining the fibrinogen level of a patient test sample with greater accuracy than prior art methods.

SUMMARY OF THE INVENTION

In accordance with the present invention, a method for determining the fibrinogen level of a blood sample is disclosed. The method comprises the steps of obtaining reference samples of blood plasmas having known fibrinogen levels in the low, normal and high ranges; sequentially performing an optically based blood coagulation test on each of said reference samples in order to determine a parameter for each of said reference samples, said parameter equalling the initial optical transmissivity of said sample under test minus a special end of reaction term corresponding to the level of light transmissivity at the point in time when the differential rate of change of optical density of said reference sample under test decreases to a fraction of its maximum value, the difference being divided by the initial optical transmissivity of each said reference sample.

A blood coagulation test is then performed on a sample of a patient's blood plasma having an unknown fibrinogen level in order to determine a parameter for the patient sample, the parameter also equalling the initial optical transmissivity of said patient sample minus a special end of reaction term corresponding to the optical transmissivity of said patient sample at the time when the differential change in optical density of the patient's sample decreases to a fraction of its previous maximum value, the difference then also being divided by the initial optical transmissivity of said sample.

Finally, the method determines the fibrinogen level of the unknown patient sample using a first linear equation if the value of the parameter of the unknown patient sample is less than the value of the parameter for the reference sample having a known fibrinogen level in the low range, a second linear equation if the value parameter of the unknown patient sample is less than the parameter of the reference sample having a known fibrinogen level in the normal range, a third linear equation if the parameter of the unknown patient sample is less than the parameter of the reference sample having a known fibrinogen level in the high range, or a fourth non-linear equation if the parameter of the unknown patient sample is greater than the parameter of the reference sample having a fibrinogen level in the high range.

DETAILED DESCRIPTION OF THE PREFERRED EMBODIMENT

Figure 1:
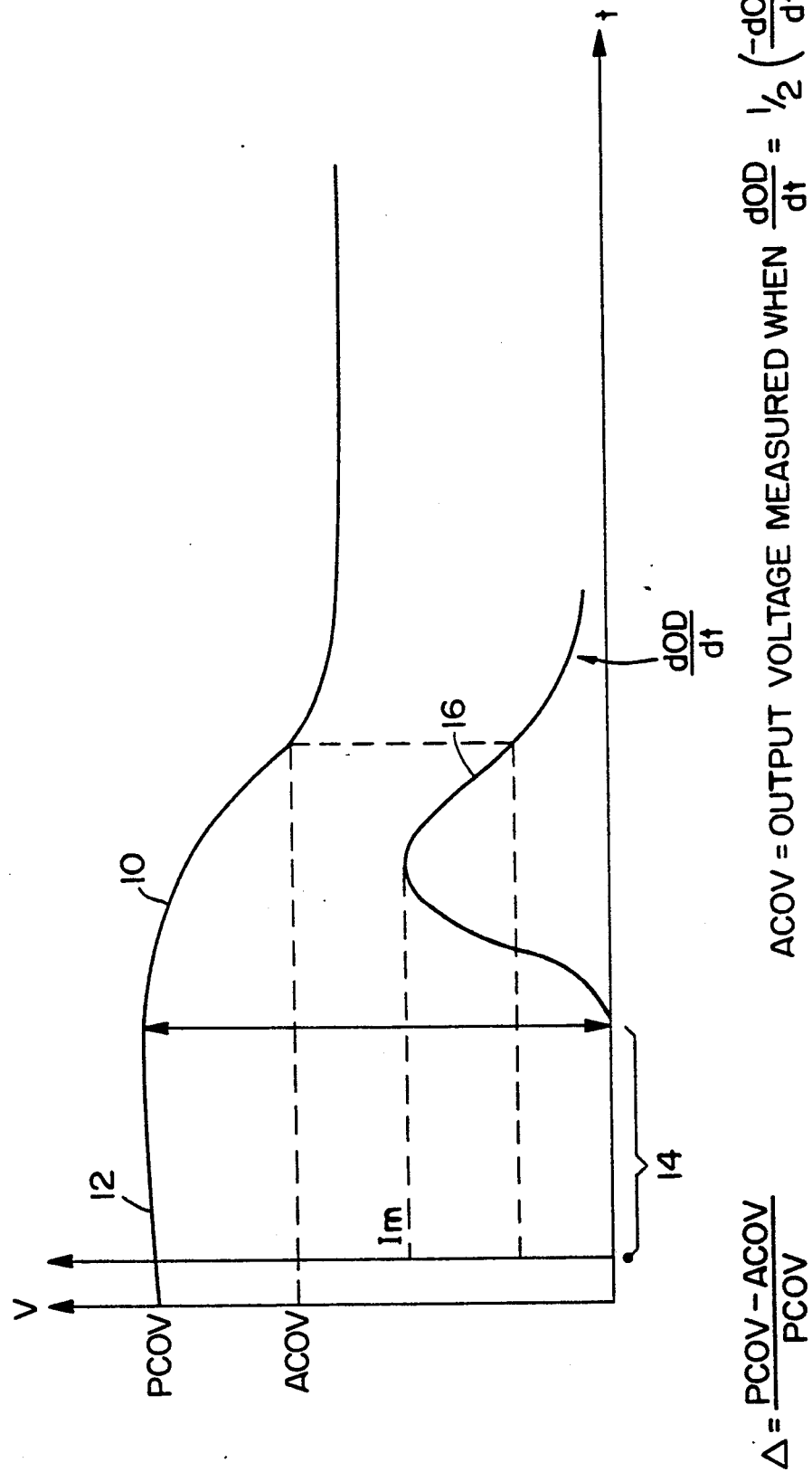
FIG. 1 is a graphical representation showing optical output voltage with respect to time and the differential change in optical density with respect to time for a PT test.

The preferred embodiment is described herein with reference to the enclosed Figures wherein the same numbers are used where appropriate. Referring to FIG. 1, a graph 10 illustrating the relationship between pre-clot optical voltage (PCOV), after-clot optical voltage (ACOV) and the first derivative of optical density with respect to time (dOD/dt) is shown. The graph reflects the well known physical phenomenon that as blood clots, the optical density of the clotting plasma increases, thereby transmitting less incident light. Thus, an optically based electronic system used to run the PT test will output a decreasing output voltage over time as the optical density of the sample plasma increases. In short, the relationship between transmissivity voltage and optical density is a reciprocal one. The pre-clot output voltage 12 is constant with respect to time for an initial period 14 corresponding to the time period preceding clot formation. In human plasma, this period is approximately 9 seconds. After 9 seconds, clot formation begins, and the optically generated output voltage decreases until the cessation of clot formation.

The lower graph 16 of FIG. 1 represents the first derivative of optical density with respect to time. It can be seen that the rate of clot formation is not linear but changes at a variable rate about a maximum value (Im). In the preferred embodiment, after clot output voltage (ACOV) represents the optical transmissivity voltage level measured at the time when the differential change in optical density decreases to one-half of its previous maximum value. While the one-half value is disclosed as the preferred embodiment, it is to be appreciated by those skilled in the art that any meaningful fraction of the maximum value can be used. This value corresponds to a point near the end of the PT test at which almost all of the clot formation activity is complete, and any remaining clotting proceeds in a predictable fashion. The parameter DELTA thus equals the change between the pre-clot output voltage (PCOV) minus after-clot output voltage (ACOV), divided by pre-clot output voltage;

$$(PCOV - ACOV)/PCOV = DELTA$$

It will be readily recognized by those skilled in the art that the DELTA parameter in the preferred embodiment is a ratio representing the percentage change in the pre-clot optical density and must lie between 0 and 1. It will also be readily recognized by those skilled in the art that plasma samples having higher fibrinogen levels will yield higher DELTA values than samples having lower fibrinogen levels.

The circuitry used in association with the present invention is now described with reference to FIGS. 3a, 3b, 3c, 4a, 4b and 5. While not shown, the circuit is associated with two conventional cuvette cells corresponding to the two channels associated with the system. In operation, LED generated electromagnetic radiation 20 in the visible or near infrared range passes through one of the two cuvette cells. The radiation is pulsed at a frequency of 200 hz. Photodiode 22 outputs a current corresponding the level of electromagnetic radiation to current to voltage amplifier 24 which outputs an analog voltage corresponding to the level of transmitted radiation. Synchronized demodulator 26 compensates for the difference in signal between the time the LED is on and off thus making the signal immune from ambient light.

The signal then goes to amplifier 28 which provides output amplification gain and frequency limitation. Capacitor 30 in combination with amplifier 32 functions as a differentiator circuit. The resulting product is the first derivative of the optical density signal. This signal will be output through switch 34 (FIG. 4b) to the analog to digital converter system and finally as a digital value to the microprocessor. The voltage signal reciprocal to optical density is input from buffer amplifier 36 into multiplexer 38.

Because the system contains two channels, two voltage signals and two first derivative signals are generated. Multiplexer 34 functions as an 8-way selector. Pins 98 and 100 receive the first derivative signals. Pins 99 and 97 received the voltage signals. The other four signals are temperature signals for controlling the heater and cooler. Multiplexer 34, thus effectively functions as a switch, and sequentially outputs one of the four test signals to digital to analog convertor (DAC) U32. DAC 40 shown in FIG. 4A outputs a 12 bit word in 3, 4 bit nibbles. Comparator 42 provides an output voltage of 0 to +10 volts. This signal then goes to comparator 41. Comparator 41 compares the input from 42 to the value output by DAC 40. The resulting signal then goes to the microprocessor. Microprocessor in association with 12 bit DAC and comparator 42 functions as a 12 bit analog to digital convertor which outputs digitized signals.

Figure 5:
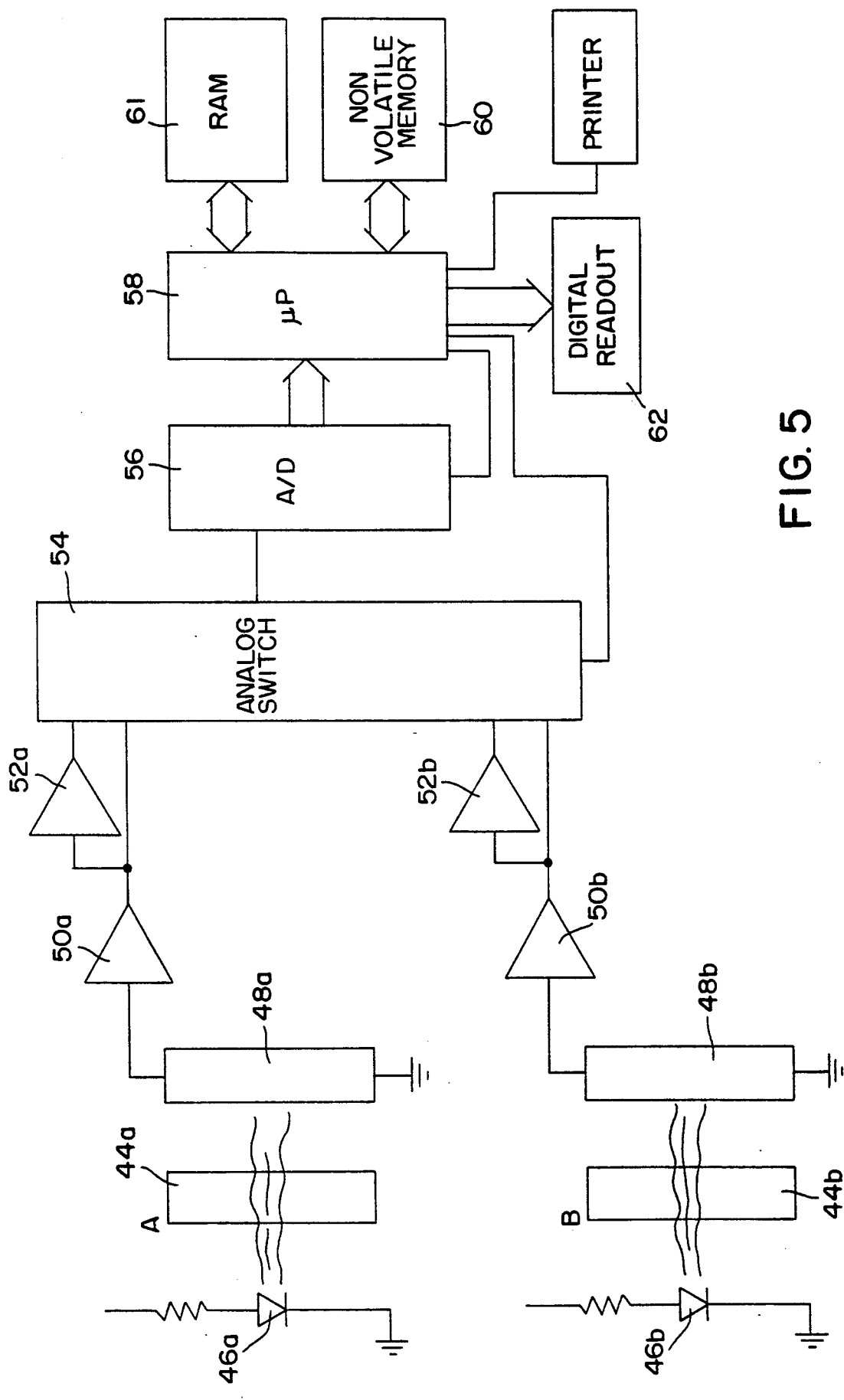
FIG. 5 is a block diagram of the apparatus utilized in the preferred embodiment.

Referring to FIG. 5, a simplified block diagram version of the circuitry described above is shown. The preferred system has A and B channels 44a, 44b corresponding to the two sample wells in the cuvette. Two LED sources 46a, 46b operating at 200 hertz propagate electromagnetic radiation toward the A and B sample wells which hold plasma mixed with thromboplastin reagent. The transmitted radiation outputs through the respective A and B channels then are then fed into respective photodiode circuits 48a, 48b which output a current proportional to the level of light transmissivity of the sample. This current is fed into a current to voltage amplifiers 50a, 50b which outputs an analog voltage reciprocal to the level of the optical density of the sample. One output of the current to voltage amplifier is fed into a differentiator amplifier 52a, 52b. The outputs from current to voltage amplifiers and differentiators for the A and B channels are then fed into an analog switch 54. Analog switch 54 sequentially feeds outputs into an analog to digital converter 56, where the analog values are digitized. The digitized signals are then fed into microprocessor 58 where they constitute input data to be used in association with three programs stored in a non-volatile memory 60 and described algorithmically below.

It is to be emphasized that the circuitry disclosed above for generating the voltages corresponding to optical density and the first derivative on optical density with respect to time is conventional. The Microsample Coagulation Analyzer model MCA 110, marketed by Bio/Data Corporation, assignee of the present application, contains the requisite circuitry to perform the operations required by the present invention. The MCA 110 is the subject matter of U.S. Pat. No. 4,695,430.

The operation of the software associated with the system is now described with reference to FIGS. 6, 7 and 8, which disclose the software algorithms in the present invention. The algorithms represent computer programs pre-stored in non-volatile memory 60 shown in FIG. 5. The following variables are defined for purposes of interpreting the algorithms of FIGS. 6, 7, and 8.

V = the measured value of the optical transmission voltage (proportional to the amount of radiation currently passing through the plasma/reagent mixture).

PCOV = the pre-clot value of V, determined at the approximate 8.5 second mark into the PT test.

dV/dT = the value of the differential rate of change of voltage with respect to time.

dV/dt(max) = the peak value of dV/dt which occurred during the test.

Figure 6:
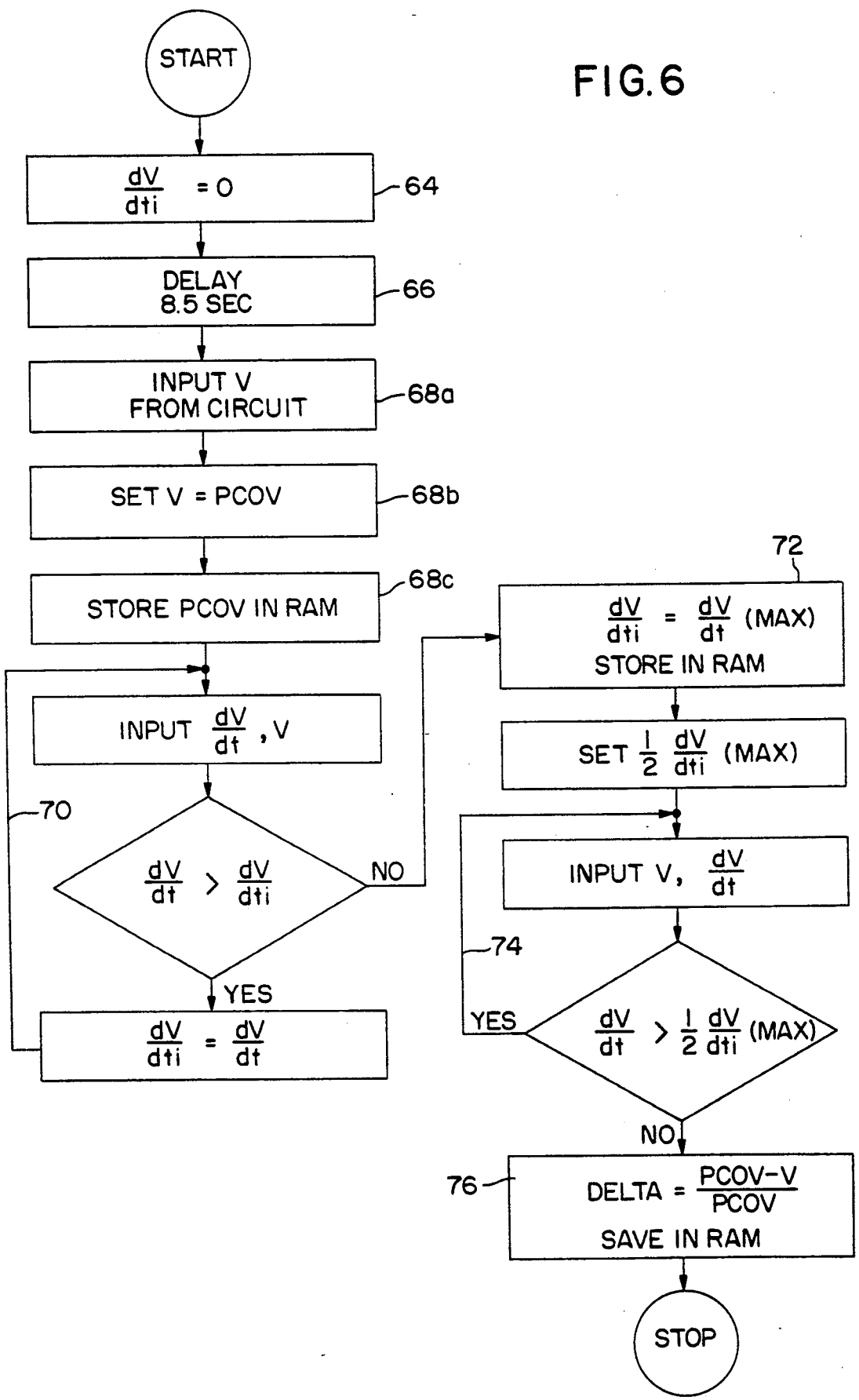
FIG. 6 is a flow chart algorithm used to calculate the DELTA parameter.

Delta = the calculated measure of clot density determined according to the algorithm of FIG. 6.

Delta−A and Delta−B = the delta values for the respective A and B channels.

Delta-AVG = the average of DELTA-A and DELTA-B.

FIBVAL(LOW)(NORMAL),(HIGH) = the calibrator plasma fibrinogen reference values in mg/dl. These quantities are keyed in by the operator and stored in non-volatile RAM 61.

DLTVAL (LOW)(NORMAL),(HIGH) are the measured delta values of the calibration plasmas.

K = a constant having a value of 0.25.

FIB = the calculated fibrinogen value of the patient test sample in mg/dl.

The determination of the DELTA parameter in association with the disclosed circuitry is now described. As shown in FIG. 5, the circuit will output digitized voltage signals reciprocal to the optical density of the sample under test. The circuitry will also output digitized signals corresponding to the change in optical density with respect to time of the sample under test. Both signals are fed to the microprocessor through the analog to digital converter. These digitized signals will approximate over time the curves shown in FIG. 1 when a PT test is run. Referring to the algorithm of FIG. 6, the software in association with microprocessor will set the initial value of dV/dt equal to zero 64. The program will then delay 8.5 seconds 66. The delay represents the period prior to the initiation of blood clotting. At this point, the voltage (V) signal input into microprocessor is measured, and stored in RAM as PCOV 68a, 68b, 68c. The digitized voltage input from analog to digital converter representing the differential change in optical density with respect to time is then also input and compared to the initial zero value. If the value is greater than zero, the input dV/dt value replaces zero and the circuit loops 70 as shown until a dV/dt(max) value is found and stored in RAM 72. The dV/dt and V signals then continue to be input and loop 74 as shown until the dV/dt signal equals ½ dV/dt (max), as noted previously. This point will occur near the end of the PT test. The voltage signal V corresponding to this point is measured and stored in RAM 61. This voltage represents ACOV. DELTA is then calculated 76 using the equation $$\text{DELTA} = \frac{PCOV - V}{PCOV}$$

The DELTA value is then stored in RAM.

Figure 2:
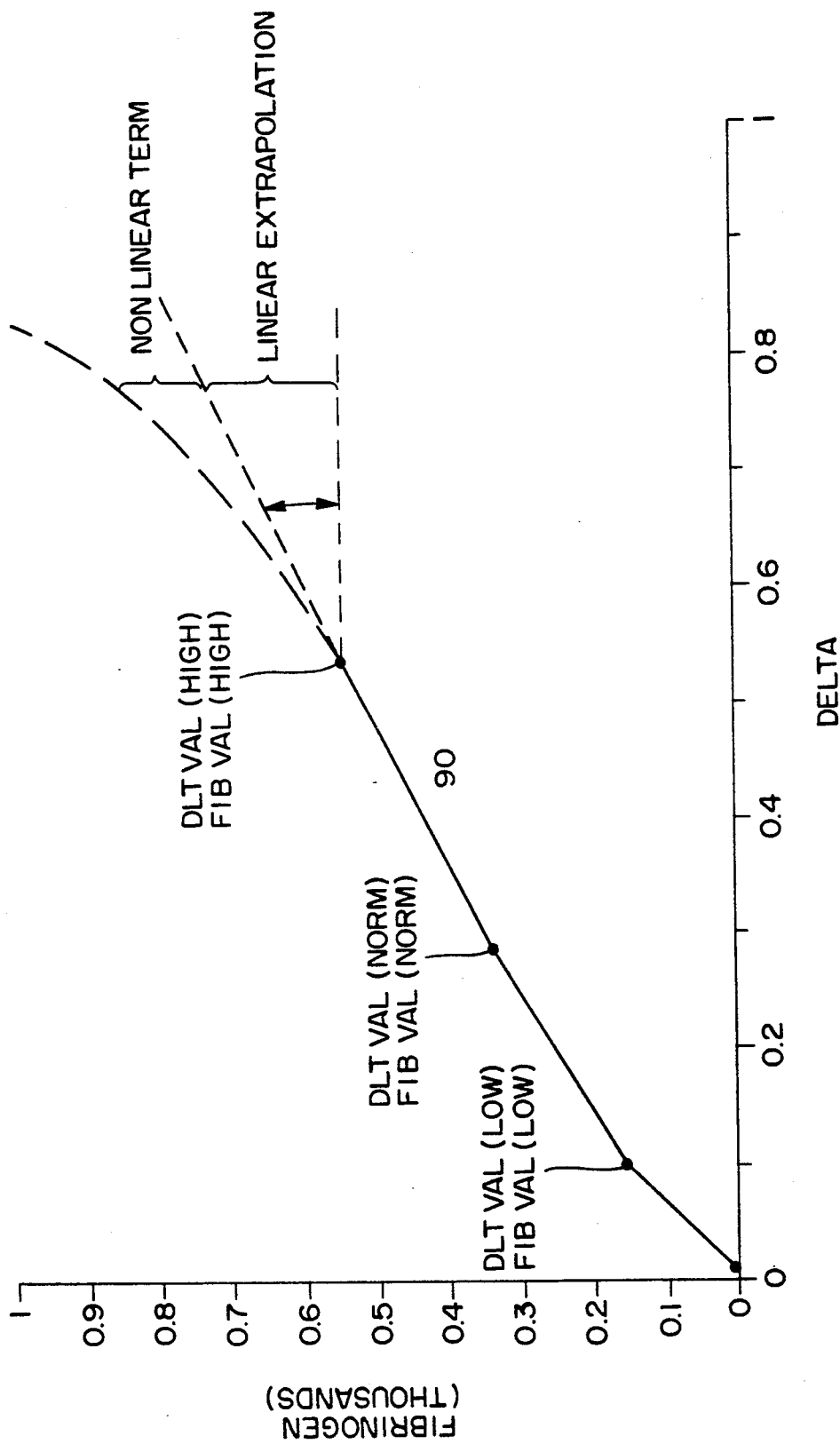
FIG. 2 illustrates the piece-wise Fibrinogen-DELTA function of the preferred embodiment with DELTA on the x-axis and Fibrinogen (in thousands) on the y-axis.
Figure 3A:
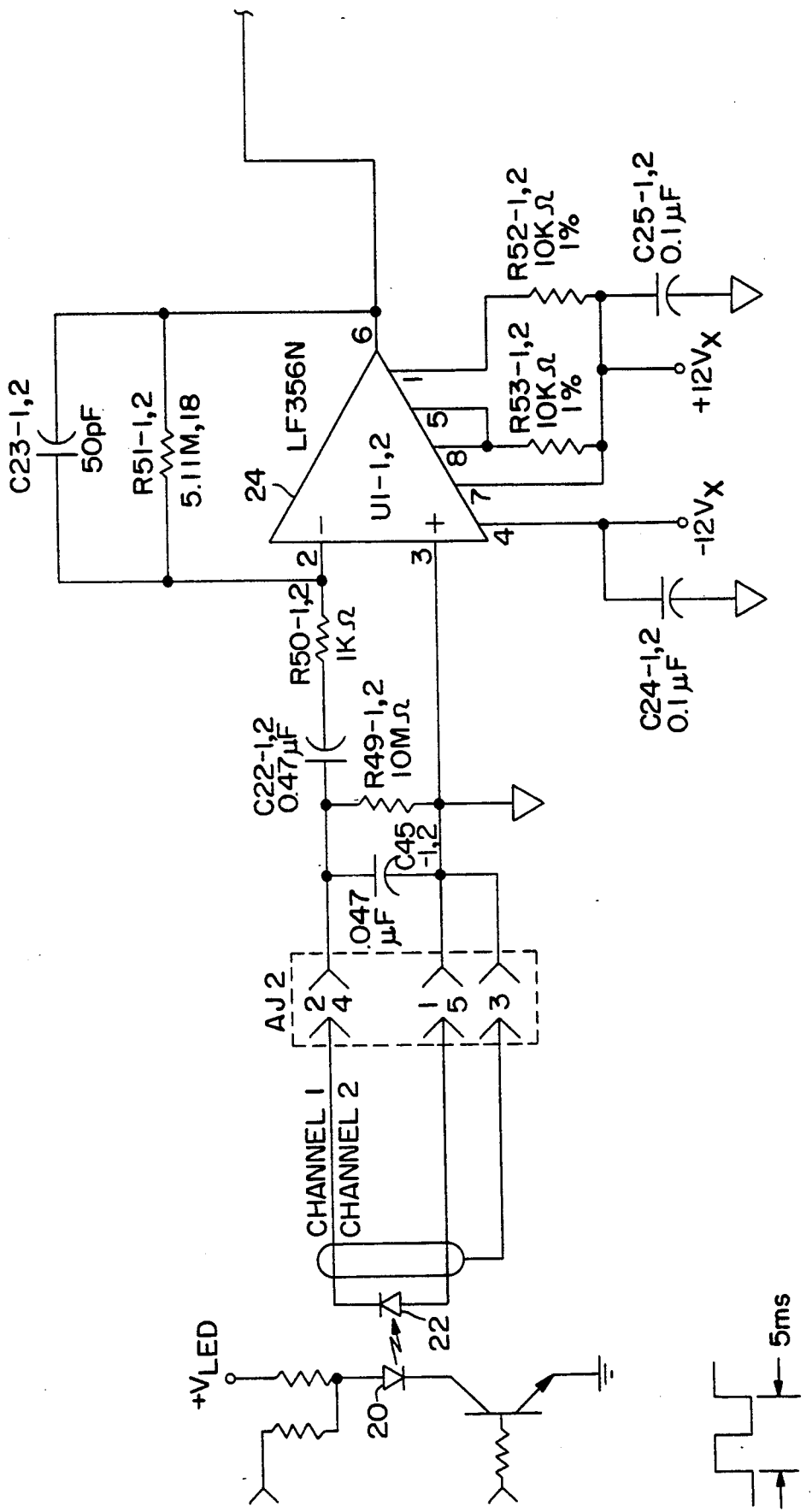
FIGS. 3a-3c illustrate the circuitry of the preferred embodiment for outputting an optical signal from a two channel input means.
Figure 3B:
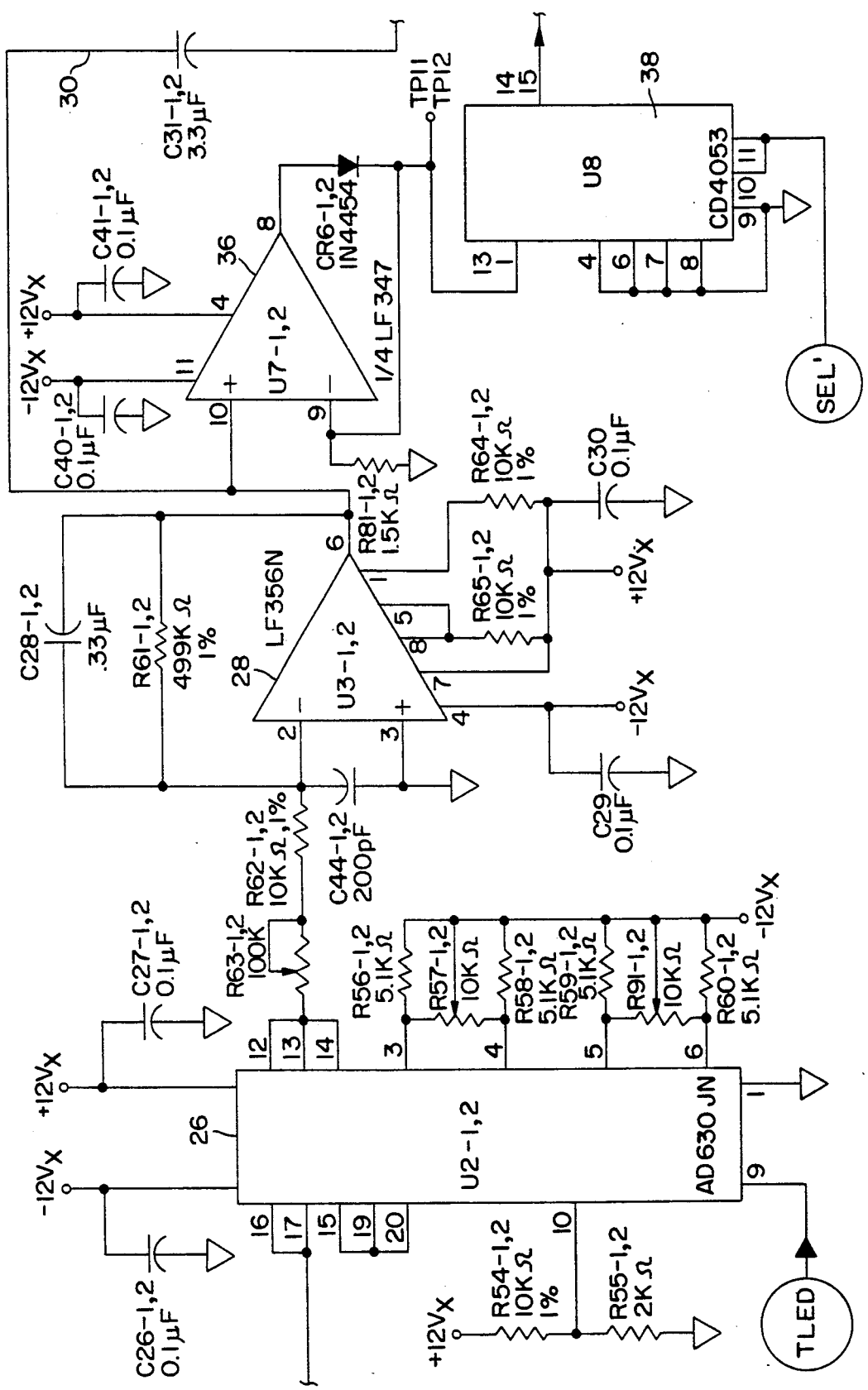
Figure 3C:
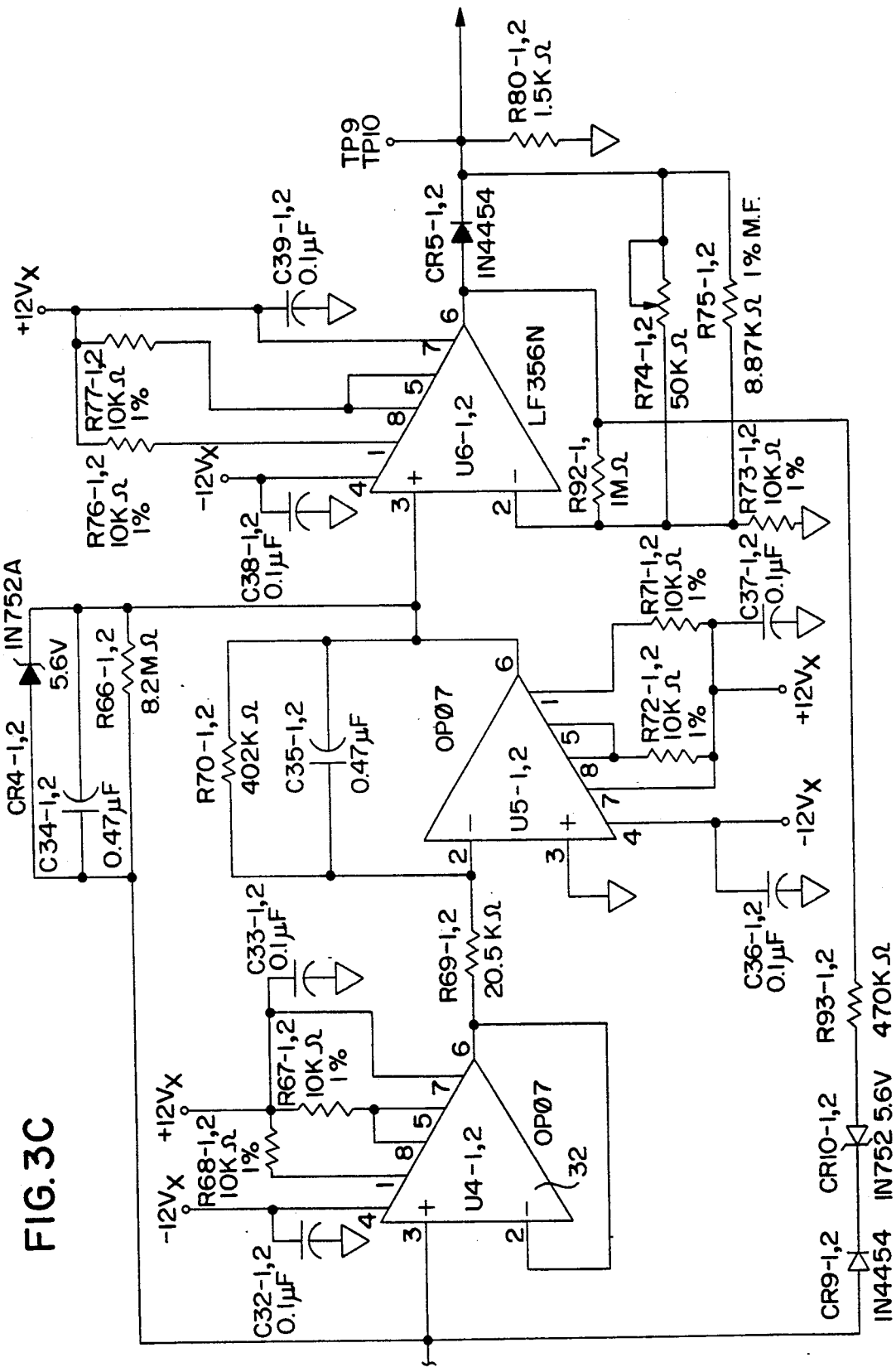
Figure 4A:
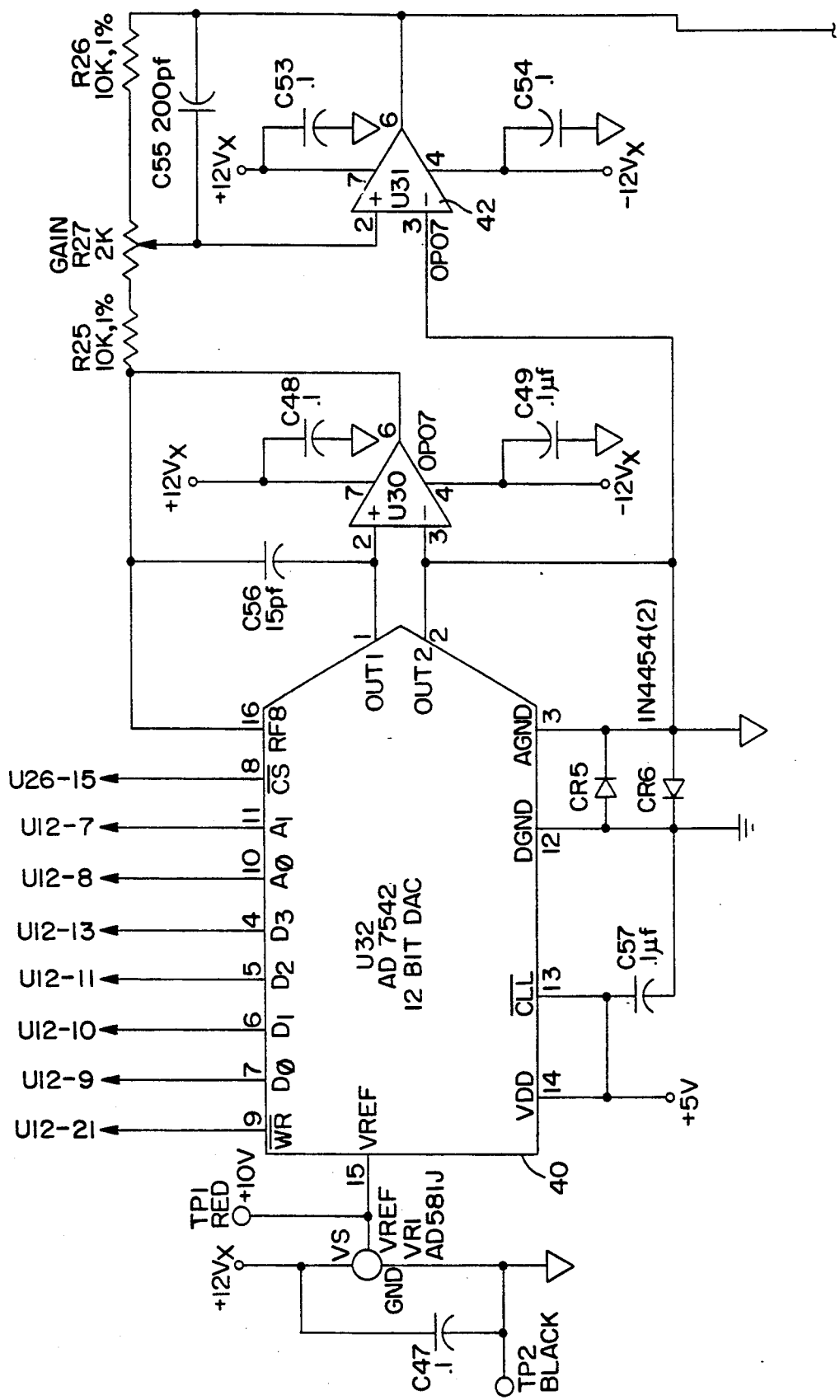
FIGS. 4a and 4b illustrates circuitry associated with the analog to digital converter for inputting digitized optical density and derivative of optical density signals to the microprocessor.
Figure 4B:
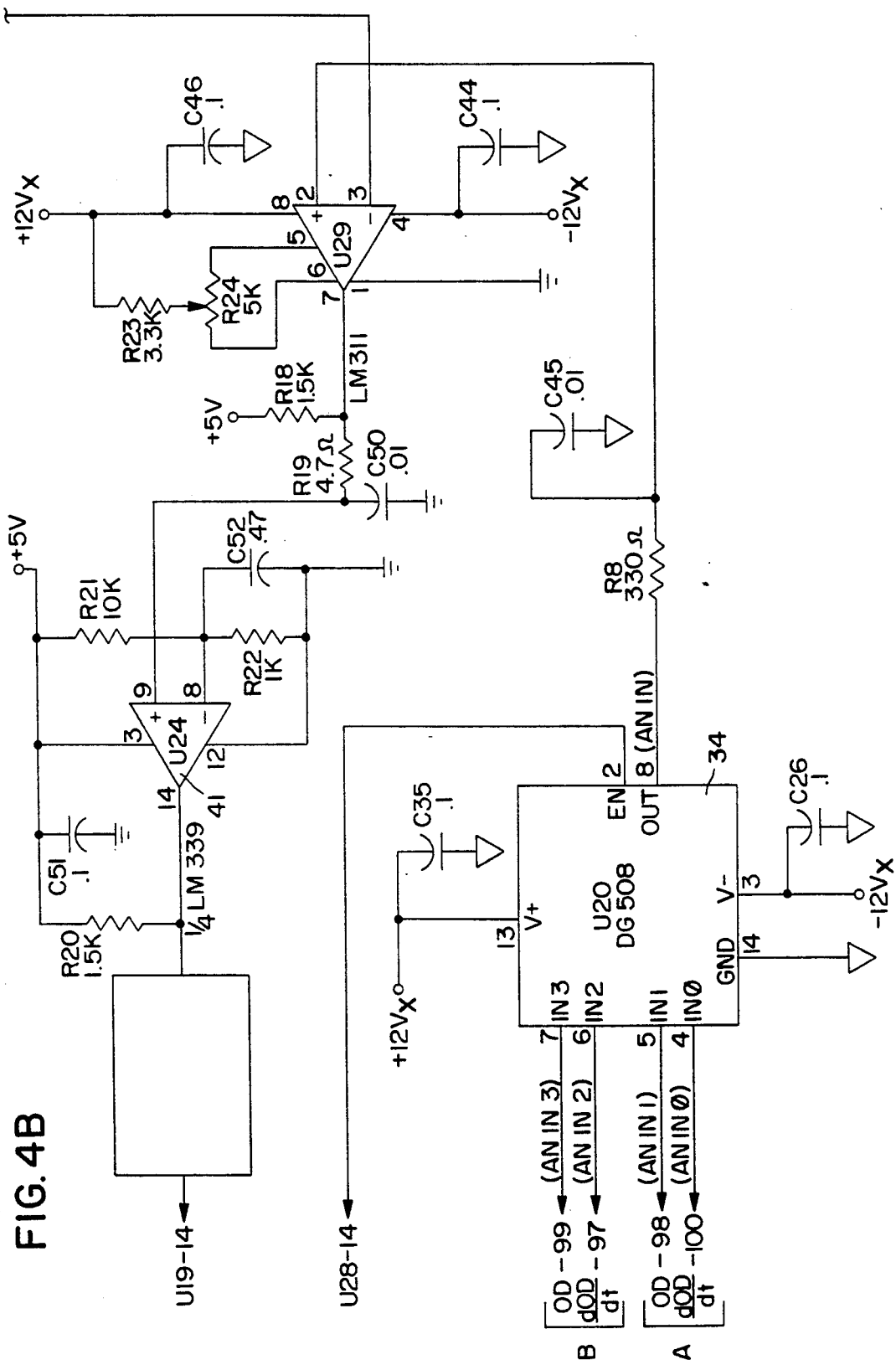

Having generally described the determination of the DELTA parameter in association with the disclosed circuitry and program of FIG. 6, the use of DELTA in the construction of a piece-wise function shown in FIG. 2 and the determination of the fibrinogen level of an unknown patient plasma sample is now described.

Initially, samples of plasmas having known fibrinogen levels are placed in the sample wells corresponding to the A and B channels. For purposes of example, samples having known fibrinogen levels of 150 mg/dl, 350 mg/dl and 550 mg/dl have been chosen. These values are pre-stored in non-volatile memory as FIBVAL (LOW), (NORM) and (HIGH). A PT test as described in FIG. 6 in conjunction with a circuitry disclosed in FIGS. 3, 4 and 5 is then run 78. DELTA values using the formula (PCOV−V)/PCOV for the A and B channels are then determined and stored as DELTA−A and DELTA−B in RAM.

Figure 7A:
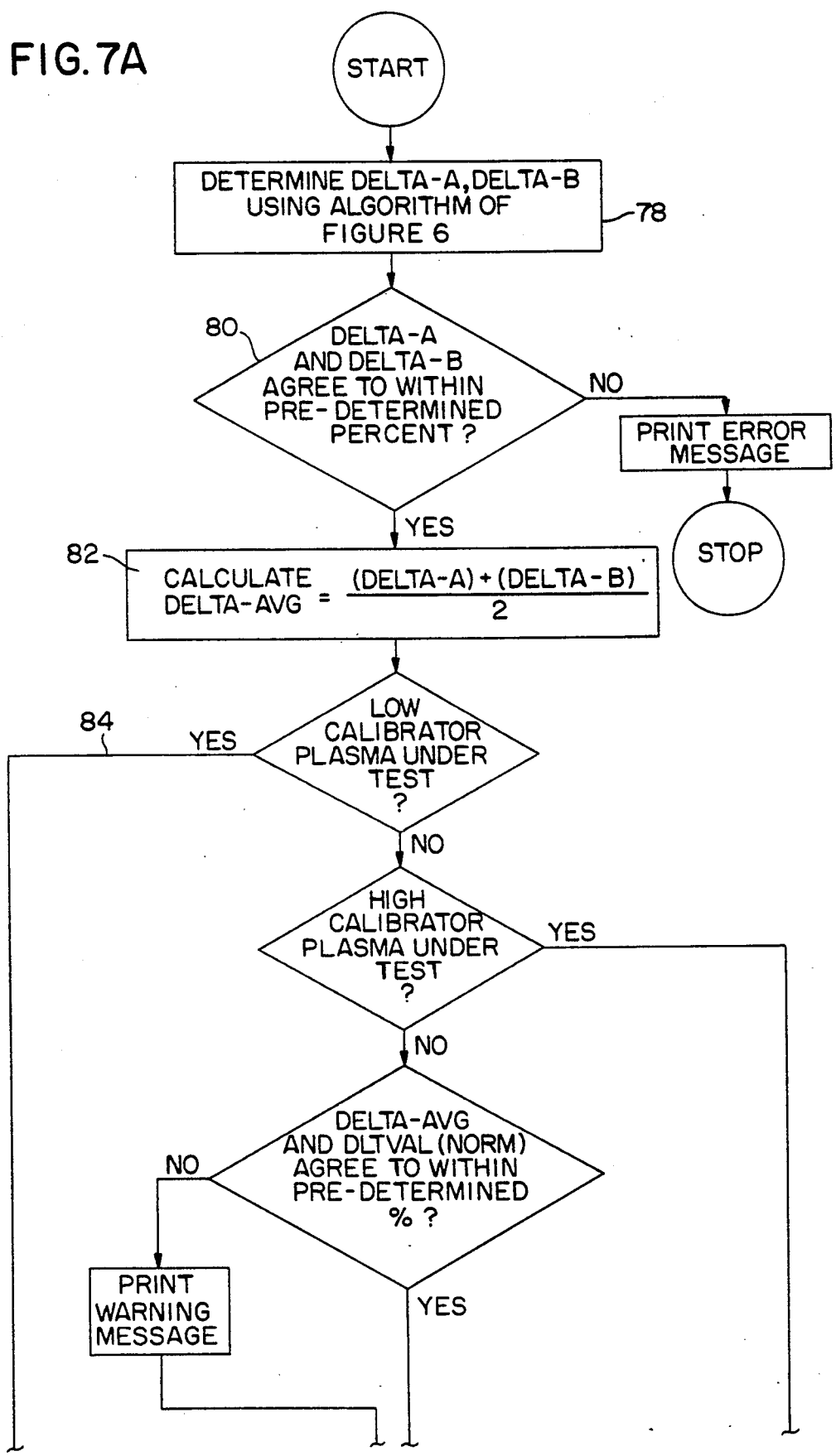
FIGS. 7A and 7B are the sequence involved in entering DELTA value of a reference sample having a known fibrinogen value and unknown DELTA value.
Figure 7B:
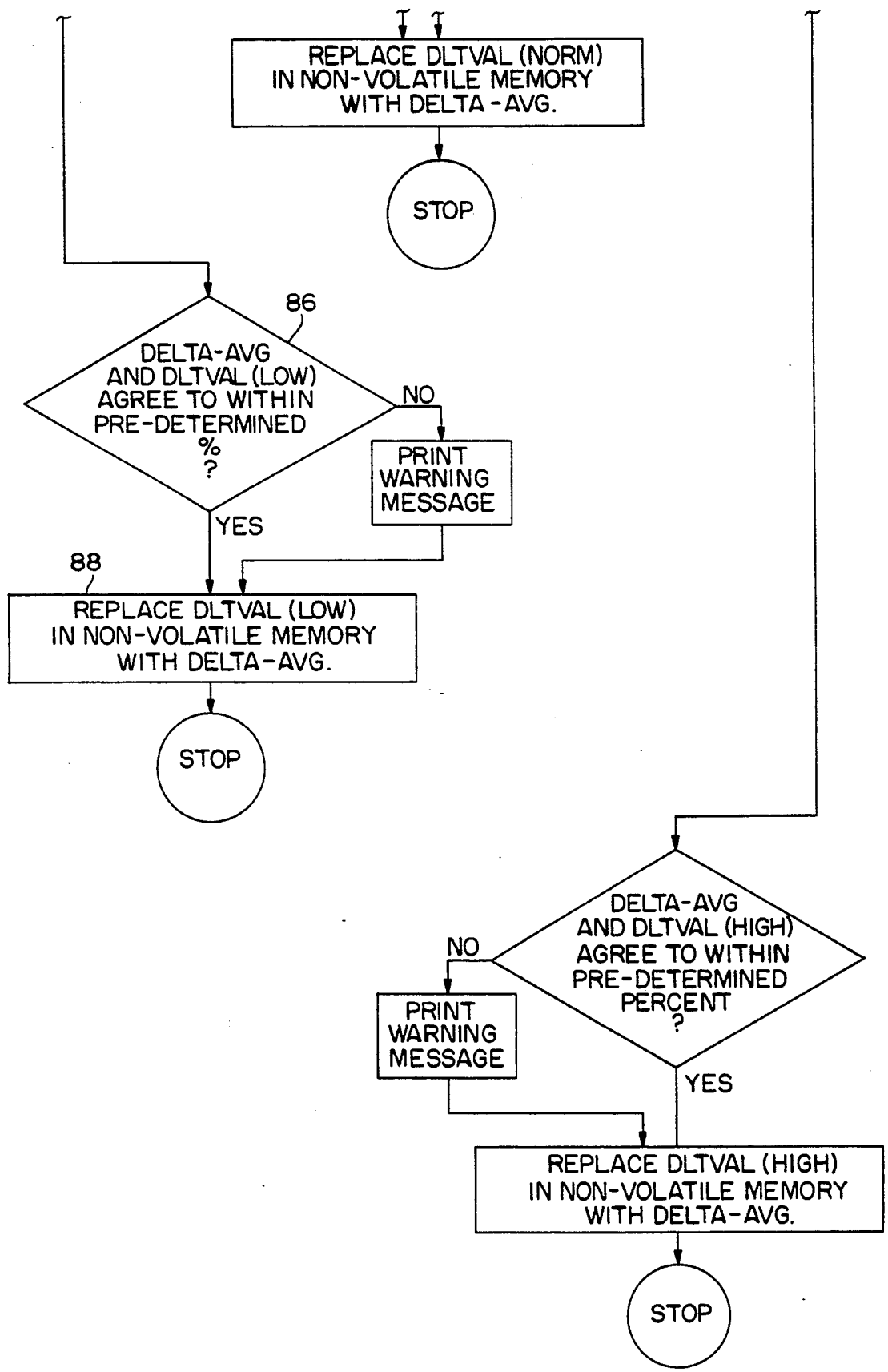
Figure 8A:
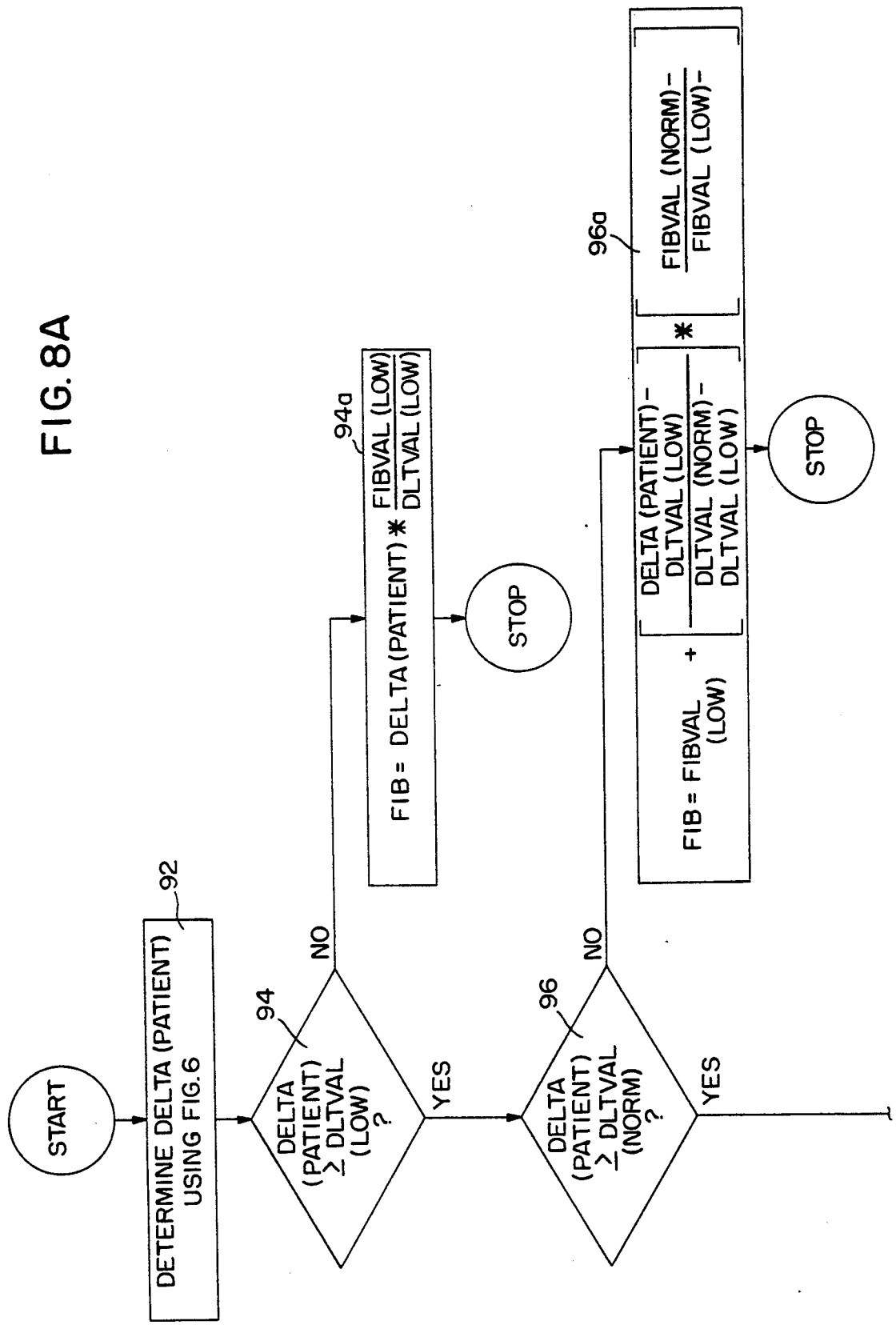
FIGS. 8A and 8B are an algorithmic representation of the calculation sequence performed upon completion of a routine PT test in which the fibrinogen value of a patient sample is calculated based on measured DELTA values and pre-stored reference data.
Figure 8B:
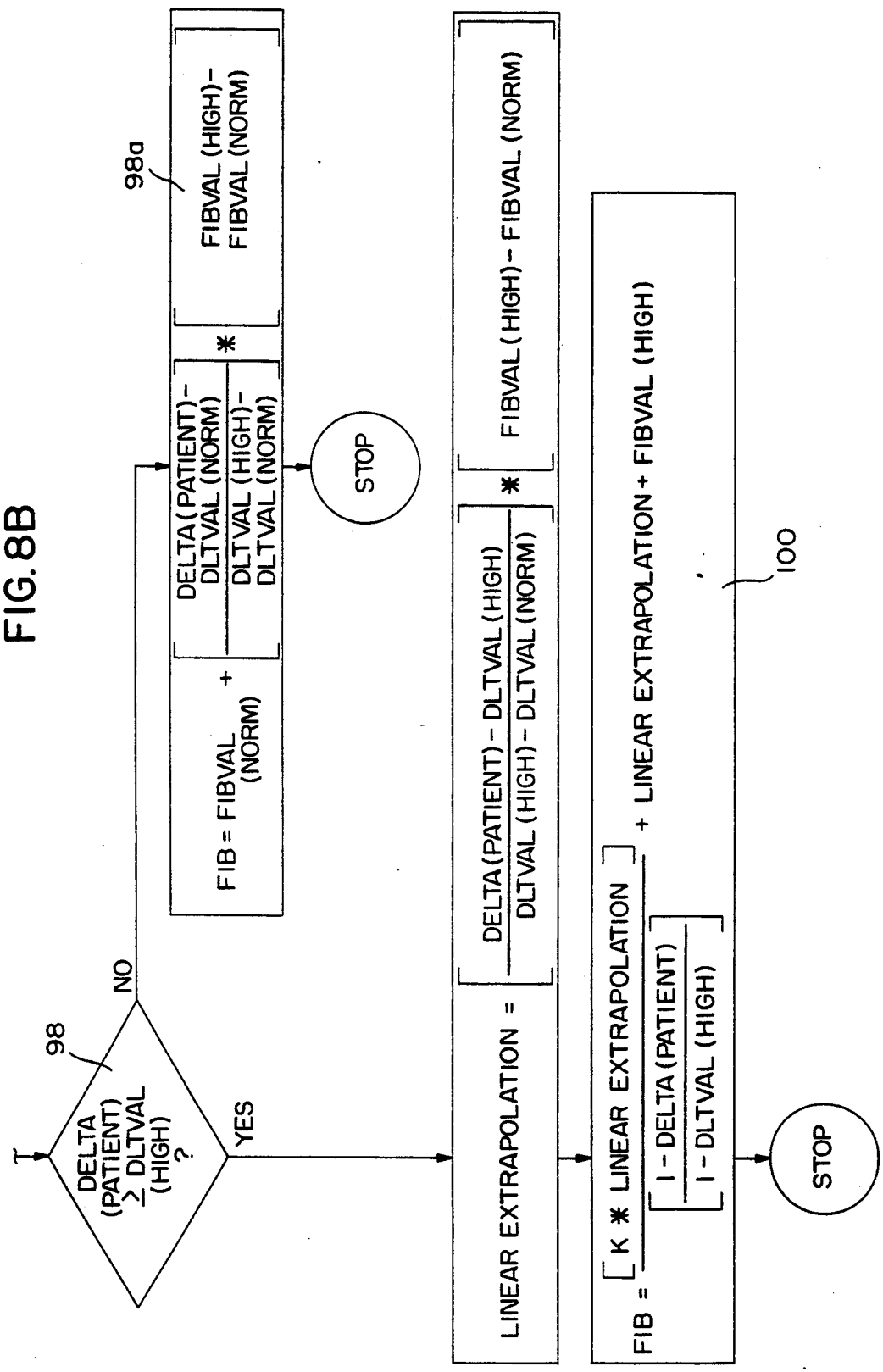

Referring now to the algorithm of FIG. 7 the values of DELTA−A and DELTA−B are first compared to determine whether they fall within a certain preset percentage of each other. This preset percentage, which ensures the statistical accuracy of the test, is variable but should preferably be a value between 10–15% 80. Assuming that the values of DELTA−A and DELTA−B fall within the preset percentage of each other, the values are averaged 82, producing the value DELTA−AVG. DELTA−AVG is then compared with the respective DLTVAL (LOW), (NORM), or (HIGH) values previously stored in non-volatile memory as previously entered calibration values. In the present example, the DELTA−AVG is based upon a test run of samples having low fibrinogen levels of 150 mg/dl. Thus, the program would proceed under the left branch 84 of the algorithm. DELTA−AVG in this example is compared for statistical accuracy with DLTVAL (LOW) 86 pre-stored in non-volatile memory 60 from a previous calibration. DLTVAL (LOW) is replaced in non-volatile memory with the DELTA−AVG value for the low fibrinogen sample 88. If the difference between DELTA AVG and DLTVAL (LOW) fall outside the pre-set statistical percentage, a warning message will be printed. This procedure is repeated for both the normal [FIBVAL (NORM)] and high [FIBVAL (HIGH)] fibrinogen level samples.

As shown in FIG. 2, a piece wise function is generated about the three DLTVAL test points generated from the samples and the three pre-stored FIBVAL values. The respective values for DLTVAL (LOW), (NORM) and (HIGH) determined experimentally in this example were 0.1, 0.3 and 0.55, respectively. Six constants are therefore stored in non-volatile memory: the three FIBVAL values corresponding to the fibrinogen values designated on the sample packages; and the three DELTVAL values empirically determined by running the PT test in accordance with the algorithm of FIG. 6:

| | | | |
|---|---|---|---|
| FIBVAL (LOW) - | 150 mg/dl | DLTVAL (LOW) - | 0.1 |
| FIBVAL (NORM) - | 350 mg/dl | DLTVAL (NORM) - | 0.3 |
| FIBVAL (HIGH) - | 550 mg/dl | DLTVAL (HIGH) - | 0.55 |

After the DELTA parameters for the piece-wise function of FIG. 2 are generated, the system is now capable of calculating the fibrinogen levels for a respective patient sample based upon the patient's individualized DELTA value. Initially, a sample of the patient's plasma is mixed with two parts thromboplastin reagent, and a PT test is run in accordance with the algorithm of FIG. 6. A DELTA(PATIENT) value is determined. Referring now to the algorithm FIG. 8, the DELTA (PATIENT) calculation is then compared to the DELTVAL(LOW) (NORM) (HIGH) values stored in memory. Depending upon the value of DELTA (PATIENT), one of four possible equations is used to calculate the fibrinogen level (FIB) of the patient. As shown, if the DELTA (PATIENT) falls in the low range, i.e. below the pre-stored value of DLTVAL (LOW) 94, the level of fibrinogen will be calculated in accordance with the following equation 94a:

$$FIB = DELTA\ (PATIENT) * \frac{FIBVAL\ (LOW)}{DLTVAL\ (LOW)}$$

It will be noted by those skilled in the art that the first equation defines a linear equation having a zero intercept.

If the value of DELTA(PATIENT) falls within the range between DLTVAL (LOW) and DLTVAL (NORM) 96, the patient's fibrinogen level is calculated in accordance with the second equation 96a:

$$FIB = FIBVAL\ (LOW) +$$

$$\frac{DELTA\ (PATIENT) - DLTVAL\ (LOW)}{DLTVAL\ (NORM) - DLTVAL\ (LOW)} * (FIBVAL\ (NORM) - FIBVAL\ (LOW))$$

If the value DELTA (PATIENT) is between DELTVAL (NORM) and DELTVAL (HIGH) 98 the third equation is utilized 98a.

$$FIB = FIBVAL\ (NORM) +$$

$$\frac{DELTA\ (PATIENT) - DLTVAL\ (NORM)}{DLTVAL\ (HIGH) - DLTVAL\ (NORM)} * (FIBVAL\ (HIGH) - FIBVAL\ (NORM))$$

It will also be noted that both the second and third equations are linear and may have non-zero intercepts.

Finally, if the value of DELTA(PATIENT) falls above DLTVAL(HIGH), a fibrinogen calculation incorporating a linear extrapolation term summed with a non-linear term which equals zero for DELTA equal to DLTVAL (HIGH) and approaches infinity for DELTA equal to one 100. This extrapolation term factors in the asymptotic nature of the fibrinogen versus optical density function and further incorporates a constant, K, which equals 0.25.

$$FIB = \frac{(K * LINEAR\ EXTRAPOLATION)}{\frac{1 - DELTA\ (PATIENT)}{1 - DLTVAL\ (HIGH)}} +$$

$$LINEAR\ EXTRAPOLATION + FIBVAL\ (HIGH);$$

where LINEAR EXTRAPOLATION =

$$\frac{DELTA\ (PATIENT) - DLTVAL\ (HIGH)}{DLTVAL\ (HIGH) - DLTVAL\ (NORM)} * (FIBVAL\ (HIGH) -$$

$$FIBVAL\ (NORM))$$

In view of the above, if a hypothetical plasma sample produces a DELTA(PATIENT) value of 0.05, the fibrinogen level would be calculated in accordance with the first equation:

$$DELTA(PATIENT) = 0.05 * FIBVAL(LOW) = 150/DLTVAL(LOW) = 0.1,$$

thereby yielding a fibrinogen level of 75 mg/dl for the patient.

In view of the foregoing, the fibrinogen level for any patient can be accurately determined with respect to the piece wise function shown in FIG. 2 which has been determined from the six test points stored in memory. The piece-wise function generated in accordance with the preferred embodiment herein accounts for the non-linear nature of the relationship between fibrinogen and change in optical density, correctly factors in a zero intercept and accounts for the asymptotic nature of DELTA as it approaches 1, thus producing more accurate fibrinogen calculations in both the low and high end ranges. The function generated in accordance with the preferred embodiment therefore produces much more accurate fibrinogen determinations than the methods utilized in the prior art.

While the invention has been disclosed and described with reference to the preferred embodiment discussed herein, it will be readily understood by those skilled in the art that numerous embodiments fall within the spirit and scope of the invention and that therefore the true scope of the invention should be defined with respect to the claims attached hereto. Specifically, although the invention has been described with reference to the prothrombin time test, the method and apparatus of the present invention are equally applicable to numerous plasma tests including recalcification, the activated partial thromboplastin time (A.P.T.T.) test, the thrombin time test, and other plasma coagulation tests.

We claim:

1. A method for determining fibrinogen level of a blood plasma sample, comprising the steps of:
   (a) obtaining reference samples of blood plasmas having known fibrinogen levels in respective low, normal and high ranges;
   (b) sequentially performing a blood coagulation test on each reference sample so as to determine a value of a parameter, said parameter equalling an initial optical density of the reference sample under test, minus a special end of reaction term corresponding to an optical density at a point in time when differential change of optical density with respect to time of said reference sample under test decreases to a fraction of its previous maximum value, the difference between the initial optical density of the reference sample and the end of reaction term of the reference sample being divided by the initial optical density of each said reference sample under test;

(c) performing a blood coagulation time test on a patient blood sample having an unknown fibrinogen level in order to determine a value of a parameter for said patient sample, said parameter equalling an initial optical density of said patient sample minus a special end of reaction term corresponding to an optical density of said patient sample at a point when the differential change of optical density with respect to time of said patient sample decreases to a fraction of its previous maximum value, the difference between the initial optical density of the patient sample and the end of reaction term of the patient sample being divided by the initial optical density of said patient sample; and (d) determining a fibrinogen level of said patient sample using a first linear equation if the value of the parameter of the unknown patient sample is less than or equal to the value of the parameter of the reference sample having a known fibrinogen level in the low range, a second linear equation if the value of the parameter of the unknown sample is less than or equal to the value of the parameter of the reference sample having a known fibrinogen level in the normal range, a third linear equation if the value of the parameter of the unknown sample is less than or equal to the value of the parameter of the reference sample having a known fibrinogen level in the high range, or a fourth non-linear equation if the value of the parameter of the unknown sample is greater than the value of the parameter for the reference sample having a fibrinogen level in the high range;

said first linear equation being a function of the value of the parameter of said unknown patient sample the fibrinogen level of said reference sample having a known fibrinogen level in the low range, and the value of the parameter for the reference sample having a fibrinogen level in the low range, and having the form $$FIB = DELTA\ (PATIENT) * \frac{FIBVAL\ (LOW)}{DLTVAL\ (LOW)};$$

said second linear equation being a function of the fibrinogen value of the reference sample having a known fibrinogen value in the low range, the value of the parameter of the unknown patient sample, the value of the parameter of the reference sample having a low fibrinogen level, the value of the parameter for the reference sample having a normal fibrinogen level, and the fibrinogen value of the reference sample having a known fibrinogen level in the normal range, and having the form $$FIB = FIBVAL\ (LOW) +$$

$$\frac{DELTA\ (PATIENT) - DLTVAL\ (LOW)}{DLTVAL\ (NORM) - DLTVAL\ (LOW)} * (FIBVAL\ (NORM) - FIBVAL\ (LOW));$$

said third linear equation being a function of the fibrinogen level of the reference sample having a known fibrinogen level in the normal range, the value of the parameter of the unknown patient sample, the value of the parameter for the reference sample having a normal fibrinogen level, the value of the parameter for the reference sample having a high fibrinogen level, and the fibrinogen level of the reference sample having a known fibrinogen level in the high range, and having the form $$FIB = FIBVAL\ (NORM) +$$

$$\frac{DELTA\ (PATIENT) - DLTVAL\ (NORM)}{DLTVAL\ (HIGH) - DLTVAL\ (NORM)} * (FIBVAL\ (HIGH) - FIBVAL\ (NORM));$$

said fourth non-linear equation being a function of a constant having a value between zero and one, a linear extrapolation term, the value of the parameter of the unknown patient sample, the value of the parameter for the reference sample having a high fibrinogen level, and the fibrinogen value of the reference sample having a known fibrinogen level in the high range, and having the form $$FIB = \frac{(K * LINEAR\ EXTRAPOLATION)}{((1 - DELTA\ (PATIENT))/(1 - DLTVAL\ (HIGH)))} +$$

$$LINEAR\ EXTRAPOLATION + FIBVAL\ (HIGH);$$

where LINEAR EXTRAPOLATION =

$$\frac{DELTA\ (PATIENT) - DLTVAL\ (HIGH)}{DLTVAL\ (HIGH) - DLTVAL\ (NORM)} * (FIBVAL\ (HIGH) - FIBVAL\ (NORM)).$$

2. A method for determining fibrinogen level of a blood plasma sample, comprising the steps of:

(a) obtaining reference samples of blood plasmas having known fibrinogen levels in low, normal and high ranges;

(b) sequentially performing a blood coagulation time test on each of said reference samples having respective known low, normal and high fibrinogen levels in order to determine a value of a parameter for each of said samples, said parameter equalling an initial optical density of said reference sample under test minus a special end of reaction term corresponding to an optical density of said reference sample under test when differential rate of change of optical density with respect to time of said reference sample decreases to a fraction of its previous maximum value, the difference between the initial optical density of the reference sample and the end of reaction term of the reference sample being divided by the initial optical density of said reference sample under test;

(c) performing a blood coagulation time test on a sample of patient blood plasma having an unknown fibrinogen level in order to determine a value of a parameter for said sample, said parameter equalling an initial optical density of said sample minus a special end of reaction term corresponding to an optical density of said patient sample at a point when the differential change of optical density with respect to time of said patient sample decreases to a fraction of its previous maximum value, the difference between the initial optical density of the patient sample and the end of reaction term of the patient sample then being divided by the initial optical density of said patient sample; and (d) determining a fibrinogen level of said patient sample using a first linear equation having a zero intercept if the value of the parameter of the unknown sample is less than the value of the parameter of the reference sample having a known fibrinogen level in the low range, a second linear equation having a non-zero intercept if the value of the parameter of the unknown sample is less than the value of the parameter of the reference sample having a known fibrinogen level in the normal range, a third linear equation having a non-zero intercept if the value of the parameter of the unknown sample is less than the value of the parameter of the reference sample having a known fibrinogen level in the high range, or a fourth non-linear equation if the value of the parameter of the unknown sample is greater than the value of the parameter for the reference sample having a fibrinogen level in the high range;

said first linear equation being a function of the value of the parameter of said unknown patient sample, the fibrinogen level of said reference sample having a known fibrinogen level in the low range, and the value of the parameter for the reference sample having a fibrinogen level in the low range, and having the form $$FIB = \text{DELTA (PATIENT)} * \frac{FIBVAL\ (LOW)}{DLTVAL\ (LOW)};$$

said second linear equation being a function of the fibrinogen value of the reference sample having a known fibrinogen value in the low range, the value of the parameter of the unknown patient sample, the value of the parameter of the reference sample having a low fibrinogen level, the value of the parameter of the reference sample having a normal fibrinogen level, and the fibrinogen value of the reference sample having a known fibrinogen level in the normal range, and having the form $$FIB = FIBVAL\ (LOW) +$$

$$\frac{\text{DELTA (PATIENT)} - DLTVAL\ (LOW)}{DLTVAL\ (NORM) - DLTVAL\ (LOW)} * (FIBVAL\ (NORM) - FIBVAL\ (LOW));$$

said third linear equation being a function of the fibrinogen level of the reference sample having a known fibrinogen level in the normal range, the value of the parameter of the unknown patient sample, the value of the parameter for reference sample having a normal fibrinogen level, the value of the parameter for the reference sample having a high fibrinogen level, and the fibrinogen level of the reference sample having a known fibrinogen level in the high range, and having the form $$FIB = FIBVAL\ (NORM) +$$

$$\frac{\text{DELTA (PATIENT)} - DLTVAL\ (NORM)}{DLTVAL\ (HIGH) - DLTVAL\ (NORM)} * (FIBVAL\ (HIGH) - FIBVAL\ (NORM));$$

said fourth non-linear equation being a function of a constant having a value between zero and one, a linear extrapolation term, the value of the parameter of the unknown patient sample, the value of the parameter for the reference sample having a high fibrinogen level, and the fibrinogen value of the reference sample having a known fibrinogen level in the high range, and having the form $$FIB = \frac{(K * \text{LINEAR EXTRAPOLATION})}{((1 - \text{DELTA (PATIENT)})/(1 - DLTVAL\ (HIGH)))} +$$

$$\text{LINEAR EXTRAPOLATION} + FIBVAL\ (HIGH);$$

where LINEAR EXTRAPOLATION =

$$\frac{\text{DELTA (PATIENT)} - DLTVAL\ (HIGH)}{DLTVAL\ (HIGH) - DLTVAL\ (NORM)} * (FIBVAL\ (HIGH) - FIBVAL\ (NORM)).$$

3. A method for determining fibrinogen level of a blood sample comprising the steps of:

(a) electronically storing values representing known fibrinogen levels of referenced blood samples having respective low, normal and high fibrinogen levels;

(b) electronically determining and storing a value of a parameter for each said reference sample in accordance with a blood coagulation time test, said parameter equalling a voltage corresponding to an optical density of said reference blood sample under test prior to the initiation of clotting minus a voltage corresponding to a special end of reaction term corresponding to an optical density when the differential change of optical density with respect to time of said reference sample decreases to a fraction of its previous maximum value, the difference between the voltage corresponding to an optical density of the reference sample and the voltage corresponding to the end of reaction term of the reference sample being divided by the voltage corresponding to optical density of the referenced blood sample under test prior to the initiation of clotting;

(c) electronically determining and storing a value of a parameter for a patient blood sample in accordance with a blood coagulation time test, said parameter equalling a voltage corresponding to an optical density of said patient blood sample prior to the initiation of clotting minus voltage corresponding to a special end of reaction term corresponding to an optical density of said patient sample when the differential change of optical density with respect of time of aid patient sample decreases to a fraction of its previous maximum value, the difference between the voltage corresponding to an optical density of the patient sample and the voltage corresponding to the end of reaction term of the patient sample being divided by the voltage corresponding to the optical density of said patient sample prior to the initiation of clotting; and (d) determining a fibrinogen level of said patient sample using a first linear equation if the value of the parameter of the patient blood sample is less than the value of the parameter of the reference sample having a known fibrinogen level in the low range, a second linear equation if the value of the parameter of the unknown sample is less than the value of the parameter of the reference sample having a known fibrinogen level in the normal range, a third linear equation if the value of the parameter of the patient blood sample is less than the value of the parameter of the reference sample having a known fibrinogen level in the high range, and a fourth non-linear equation the value of the parameter of the unknown sample is greater than the value of the parameter for the reference sample having a fibrinogen level in the high range;

said first linear equation being a function of the value of the parameter of said unknown patient sample, the fibrinogen level of said reference sample having a known fibrinogen level in the low range, and the value of the parameter for the reference sample having a fibrinogen level in the low range, and having the form $$FIB = \text{DELTA (PATIENT)} * \frac{FIBVAL\ (LOW)}{DLTVAL\ (LOW)};$$

said second equation being a function of the fibrinogen value of the reference sample having a known fibrinogen value in the low range, the value of the parameter of the unknown patient sample, the value of the parameter of the reference sample having a low fibrinogen level, the value of the parameter of the reference sample having a normal fibrinogen level, and the fibrinogen value of the reference sample having a known fibrinogen level in the normal range, and having the form $$FIB = FIBVAL\ (LOW) +$$

$$\frac{DELTA\ (PATIENT) - DLTVAL\ (LOW)}{DLTVAL\ (NORM) - DLTVAL\ (LOW)} * (FIBVAL\ (NORM) - FIBVAL\ (LOW));$$

said third linear equation being a function of the fibrinogen level of the reference sample having a known fibrinogen level in the normal range, the value of the parameter of the unknown patient sample, the value of the parameter for reference sample having a normal fibrinogen level, the value of the parameter for the reference sample having a high fibrinogen level, and the fibrinogen level of the reference sample having a known fibrinogen level in the high range, and having the form $$FIB = FIBVAL\ (NORM) +$$

$$\frac{DELTA\ (PATIENT) - DLTVAL\ (NORM)}{DLTVAL\ (HIGH) - DLTVAL\ (NORM)} * (FIBVAL\ (HIGH) - FIBVAL\ (NORM));$$

said fourth non-linear equation being a function of a constant having a value between zero and one, a linear extrapolation term, the value of the parameter of the unknown patient sample, the value of the parameter for the reference sample having a high fibrinogen level, and the fibrinogen value of the reference sample having a known fibrinogen level in the high range, and having the form $$FIB = \frac{(K * \text{LINEAR EXTRAPOLATION})}{((1 - \text{DELTA (PATIENT)})/(1 - DLTVAL\ (HIGH)))} +$$

$$\text{LINEAR EXTRAPOLATION} + FIBVAL\ (HIGH);$$

where LINEAR EXTRAPOLATION =

$$\frac{DELTA\ (PATIENT) - DLTVAL\ (HIGH)}{DLTVAL\ (HIGH) - DLTVAL\ (NORM)} * (FIBVAL\ (HIGH) - FIBVAL\ (NORM)).$$

* * * * *